US006562386B2

(12) United States Patent
Ruan et al.

(10) Patent No.: US 6,562,386 B2
(45) Date of Patent: May 13, 2003

(54) METHOD AND APPARATUS FOR NON-THERMAL PASTEURIZATION

(75) Inventors: R. Roger Ruan, Arden Hills, MN (US); Hongbin Ma, St. Paul, MN (US); Mingliang Zhang, St. Paul, MN (US); Paul L. Chen, Roseville, MN (US); Duane Oyen, Maple Grove, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 17 days.

(21) Appl. No.: 09/850,284

(22) Filed: May 7, 2001

(65) Prior Publication Data
US 2003/0026877 A1 Feb. 6, 2003

(51) Int. Cl.[7] .......................... A23L 3/3409; B01J 19/08
(52) U.S. Cl. .................. 426/237; 426/247; 422/186.04; 422/22; 204/164
(58) Field of Search ................................ 426/237, 247; 422/186.04, 22; 204/164

(56) References Cited

U.S. PATENT DOCUMENTS

| 2,345,798 A | 4/1944 | Daily |
| 3,865,733 A | 2/1975 | Taylor ........................ 250/532 |
| 3,898,468 A | 8/1975 | Guerin ........................ 250/535 |

(List continued on next page.)

FOREIGN PATENT DOCUMENTS

| DE | 43 32 866 A1 | 3/1995 |
| DE | 196 35 231 A1 | 3/1998 |
| EP | 1271554 A1 | 11/1986 |
| EP | 1495286 A | 7/1989 |
| EP | 19717169 A1 | 10/1998 |
| GB | 2316017 | 2/1998 |
| JP | 59-69404 | 4/1984 |
| JP | 2-211218 | 8/1990 |
| JP | 2-211219 | 8/1990 |
| JP | 4-122417 | 4/1992 |
| JP | 4-247218 | 9/1992 |
| JP | 5-15736 | 1/1993 |
| JP | 07 256056 | 10/1995 |
| JP | 10-118448 | 5/1998 |
| JP | 10-235138 | 8/1998 |
| JP | 10-235138 | 9/1998 |
| RU | 002140238 | 11/1996 |
| WO | WO 95/09256 | 4/1995 |
| WO | 980342 | 1/1998 |
| WO | WO 01/52910 A1 | 7/2001 |

OTHER PUBLICATIONS

Kimberly Kelly Wintenberg et al., Air Filter Sterilization Using a One Atmosphere Uniform Glow Discharge Plasma (the Volfilter), IEEE Transactions on Plasma Science, Feb. 2000, vol. 28, No. 1.

Thomas C. Montie et al., An Overview of Research Using the one Atmosphere Uniform Glow Discharge Plasma (Oaugdp) For Sterilization of Surfaces and Materials, IEEE Transactions on Plasma Science, Feb. 2000, vol. 28, No. 1.

J. Reece Roth et al., A Remote Exposure Reactor (RER) for Plasma Processing and Sterilization by Plasma Active Species at One Atmosphere, IEEE Transactions on Plasma Science, Feb. 2000, vol. 28., No. 1.

Joseph G. Birmingham et al., Bacterial Decontamination Using Ambient Pressure Nonthermal Discharge, IEEE Transactions on Plasma Science, Feb. 2000, vol. 28, No. 1.

K. Kelly–Wintenberg et al., Use of a One Atmosphere Uniform Glow Discharge Plasma to Kill a Broad Spectrum of Microorganisms, J. Vac. Sci. Technol., Jul./Aug. 1999.

Primary Examiner—Nina Bhat
(74) Attorney, Agent, or Firm—Westman, Champlin & Kelly

(57) ABSTRACT

A method and apparatus are provided for at least partially sterilizing a liquid that has pathogens living in the liquid. The liquid comprising living pathogens is placed in a reaction volume, and a non-thermal plasma is generated within the reaction volume to thereby kill at least a portion of the pathogens within the liquid.

28 Claims, 6 Drawing Sheets

U.S. PATENT DOCUMENTS

| | | | | |
|---|---|---|---|---|
| 3,970,905 | A | 7/1976 | Iyoh et al. | 317/262 E |
| 4,244,712 | A | 1/1981 | Tongret | 55/124 |
| 4,391,773 | A | 7/1983 | Flanagan | 422/22 |
| 4,863,701 | A | 9/1989 | McMurray | 422/186.08 |
| 5,304,486 | A | 4/1994 | Chang | 435/287 |
| 5,326,530 | A | 7/1994 | Bridges | 422/22 |
| 5,370,846 | A | 12/1994 | Yokomi et al. | 422/186.07 |
| 5,411,713 | A | 5/1995 | Iwanaga | 422/186.15 |
| 5,427,747 | A | 6/1995 | Kong et al. | 422/186 |
| 5,458,748 | A | 10/1995 | Breault et al. | 204/177 |
| 5,516,493 | A | 5/1996 | Bell et al. | 422/186.07 |
| 5,549,874 | A | 8/1996 | Kamiya et al. | 422/186.04 |
| 5,603,893 | A | 2/1997 | Gundersen et al. | 422/22 |
| 5,637,198 | A | 6/1997 | Breault | 204/165 |
| 5,670,122 | A | 9/1997 | Zamansky et al. | 423/210 |
| 5,681,533 | A | 10/1997 | Hiromi | 422/121 |
| 5,695,619 | A | 12/1997 | Williamson et al. | 204/165 |
| 5,711,147 | A | 1/1998 | Vogtlin et al. | 60/274 |
| 5,746,984 | A | 5/1998 | Hoard | 422/169 |
| 5,750,823 | A * | 5/1998 | Wofford et al. | 588/210 |
| 5,759,497 | A | 6/1998 | Kuzumoto et al. | 422/186.07 |
| 5,822,981 | A | 10/1998 | Williamson et al. | 60/275 |
| 5,836,154 | A | 11/1998 | Williamson et al. | 60/275 |
| 5,843,288 | A * | 12/1998 | Yamamoto | 204/164 |
| 5,843,383 | A | 12/1998 | Williamson et al. | 422/186.04 |
| 5,855,855 | A | 1/1999 | Williamson et al. | 422/186.04 |
| 5,871,703 | A | 2/1999 | Alix et al. | 423/210 |
| 5,876,663 | A | 3/1999 | Laroussi | 422/23 |
| 5,891,409 | A | 4/1999 | Hsiao et al. | 423/239.1 |
| 5,893,267 | A * | 4/1999 | Vogtlin et al. | 60/274 |
| 5,895,558 | A | 4/1999 | Spence | 204/164 |
| 5,895,632 | A | 4/1999 | Nomura et al. | 422/186.04 |
| 5,904,905 | A | 5/1999 | Dolezal et al. | 422/186.04 |
| 6,030,506 | A * | 2/2000 | Bittenson et al. | 204/164 |
| 6,096,564 | A * | 8/2000 | Denes et al. | 438/1 |
| 6,146,599 | A | 11/2000 | Ruan et al. | 422/186.04 |
| 6,171,450 | B1 | 1/2001 | Behnisch et al. | 204/164 |
| 6,176,078 | B1 | 1/2001 | Balko et al. | 60/274 |
| 6,228,330 | B1 * | 5/2001 | Herrmann et al. | 422/186.05 |

* cited by examiner

METHOD AND APPARATUS FOR NON-THERMAL PASTEURIZATION

BACKGROUND OF THE INVENTION

The present invention relates to non-thermal pasteurization and/or sterilization of a living-mammal-instillable liquid to destroy live pathogens living in the liquid.

Various methods of pasteurizing liquids such as liquid foods, fermentation broth, biological fluids, blood products, medicines, vaccines, etc., have been used for destroying live pathogens, including bacteria, viruses and fungi, living in the liquids. However, these methods typically generate heat during the pasteurization process and may also introduce impurities depending on the process. This heat can easily damage active components, ingredients or other desirable characteristics of the liquid, such as food nutrients and sensory attributes, including flavors, aromas and colors. If these products are thermally processed, they will become unacceptable or their commercial values will be greatly reduced. In the case of biological fluids living cells may be altered or damaged. Therefore, a number of minimal thermal processes have been developed for some of these applications, including ultra-filtration, ozonation, pulsed ultraviolet light, irradiation, high hydrostatic pressure (HHP) and pulsed electric field (PEF) discharge.

Of these methods, PEF discharge has been shown to be very effective for killing bacteria within liquids. PEF discharge is considered to be one of the premier new technologies with a great potential of replacing thermal, chemical and other pasteurization and sterilization technologies for the treatment of liquid foods and pharmaceuticals. However, there are a number of drawbacks of the PEF discharge technology. For example, ohmic heating occurs during the PEF discharge, which causes the temperature of the liquid being treated to rise. Hence, a cooling system must be used in order to maintain the liquid at a low temperature. A significant amount of energy is wasted with unwanted heating and cooling of the liquid. Also, the requirement of a cooling system adversely increases the time required to treat the liquid. In addition, the PEF electrodes are immersed directly in the liquid. Since the electrodes contact the liquid, they are regarded as a major contamination source to the liquid due to oxidation of the electrodes during discharge. The electrodes must therefore be replaced regularly, which increases maintenance time and costs.

Improved methods of non-thermal pasteurization are desired for pasteurizing liquids without degrading the natural characteristics of the liquids.

SUMMARY OF THE INVENTION

One aspect of the present invention is directed to a method for at least partially sterilizing a liquid that has pathogens living in the liquid. The method includes placing the liquid comprising living pathogens in a reaction volume, and generating a non-thermal plasma within the reaction volume to thereby kill at least a portion of the pathogens within the liquid.

Non-thermal plasma species are generated by applying a high voltage, low current charge between two opposite polarity electrodes. The non-thermal plasma species often include electrically neutral gas molecules, charged particles in the form of positive ions, negative ions, free radicals and electrons, and quanta of electromagnetic radiation (photons). These non-thermal plasma species are highly reactive and are effective in killing live pathogens, such as bacteria, viruses and fungi, living in the liquid being treated.

Another aspect of the present invention is directed to a liquid food pasteurization apparatus. The apparatus includes a liquid food input, a treatment flow path coupled to the liquid food input, a pump, a gas injector and a non-thermal plasma reactor. The pump is coupled to the treatment flow path for pumping liquid food from the liquid food input through the treatment flow path. The gas injector is coupled in the treatment flow path and has a gas inlet for receiving a gas to be injected into the liquid food. The non-thermal plasma reactor is also coupled in the treatment flow path and includes a liquid food inlet, a liquid food outlet, a reaction volume between the liquid food inlet and the liquid food outlet, and at least one non-thermal plasma electrode adjacent to the reaction volume. Each non-thermal plasma electrode is isolated physically and electrically from the flow path by a dielectric barrier.

Another aspect of the present invention is directed to a liquid food pasteurization apparatus, which includes a liquid food input, a gas source and a non-thermal plasma reactor. A liquid food comprising living pathogens is received through the liquid food input. Gas bubbles are introduced from the gas source into the liquid food received from the liquid food input to produce a mixture of the liquid food and the gas bubbles. The non-thermal plasma reactor receives the mixture of the liquid food and the gas bubbles within a reaction volume and generates a non-thermal plasma within the reaction volume to thereby kill at least a portion of the pathogens within the liquid food.

DETAILED DESCRIPTION OF THE PREFERRED EMBODIMENTS

Figure 1:
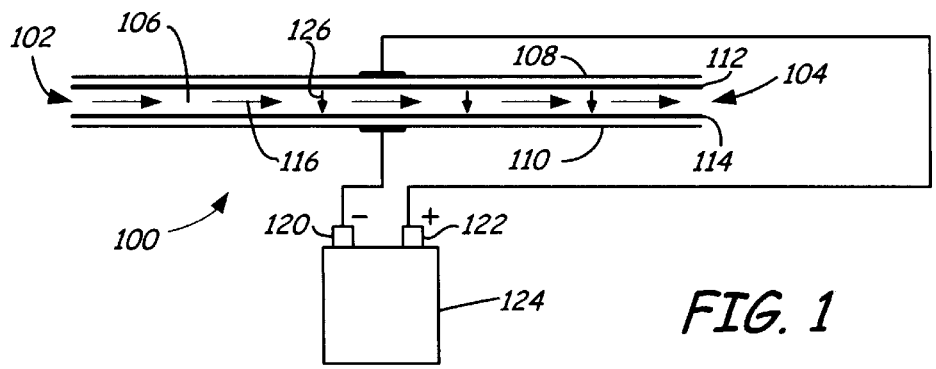
FIG. 1 is a diagrammatic view of a "silent type", volume discharge non-thermal plasma reactor, which can be used for pasteurizing liquids to destroy live pathogens living in the liquids.

FIG. 1 is a diagrammatic view of a "silent type", volume discharge non-thermal plasma reactor 100, which can be used for pasteurizing and/or at least partially sterilizing living-mammal-instillable liquids to kill live pathogens living in the liquids. Non-thermal plasma reactor 100 includes a liquid inlet 102, a liquid outlet 104, a reaction volume 106 between liquid inlet 102 and liquid outlet 104, electrodes 108 and 110, and dielectric barriers 112 and 114. Flow path 116 indicates the liquid flow path from inlet 102 to outlet 104, through reaction volume 106. Each of the electrodes 108 and 110 is physically and electrically isolated from the liquid in flow path 112 by a respective one of the dielectric barriers 112 and 114.

Dielectric barriers 112 and 114 are separated from one another by a gap, which defines the effective width of reaction volume 106. Dielectric barriers 112 and 114 can include Teflon, glass, ceramic or epoxy resin, for example. Other insulating materials can also be used. In one embodiment, each electrode 108 and 110 is embedded within an epoxy resin. The discharge gap between electrodes 108 and 110 can be sized to suit a particular application. For example, electrodes 108 and 110 can be separated by a distance of up to 30 centimeters. A larger gap can be used if voltage and insulation conditions. permit. In one particular embodiment, electrodes 108 and 110 are separated by 10 millimeters, with an effective gap between dielectric layers 112 and 114 of about 7 millimeters.

Electrodes 108 and 100 can have a variety of configurations. For example in the embodiment shown in FIG. 1, electrodes 108 and 110 are each formed of a thin, planar sheet of conductive metal, such as a copper foil. Other conductive structures can also be used such as a conductive mesh, wire or strip. The combination of electrodes 108 and 110 can have a variety of different types, such as plate-to-plate, mesh-to-mesh, plate-to-wire, wire-to-wire, plate-to-mesh and wire-to-mesh, for example. The shapes of electrodes 108 and 110 can also be varied. For example, electrodes 108 and 110 can be arranged coaxially with one another, wherein the outer electrode is tubular and the inner electrode is either tubular or a wire. Other arrangements can also be used. However, in each arrangement, both electrodes 108 and 110 are physically and electrically isolated from the liquid in the reaction volume by a dielectric barrier in order to prevent an electrical conduction path through the liquid and contamination of the liquid due to contact with the electrodes.

High voltage power supply 124 supplies power to electrodes 108 and 110. Electrode 108 is electrically coupled to a first terminal 120 of power supply 124, and electrode 110 is electrically coupled to a second terminal 122 of power supply 124. One of the electrodes 108 and 110 serves a ground electrode, such as electrode 110, and the other, such as electrode 108, serves as a high voltage electrode. Power supply 124 can include a direct-current (DC) or an alternating-current (AC) power supply that is capable of producing a voltage across electrodes 108 and 110 so as to form an electric discharge-path, shown by arrows 126, across reaction volume 106. In one embodiment, the voltage potential generated between electrodes 108 and 110 is in the range of 1 kV–35 kV, for example. Other voltage ranges can also be used, such as voltage ranges between 1 kV and 500 kV. Power supply 124 can be operated at either low or high frequencies and can produce pulses with a single polarity or can produce bipolar pulses.

With electrodes 108 and 110 having opposite polarity, electrodes 108 and 110 generate a strong electrical field across reaction volume 106. The strong electrical field is applied to gas in the liquid, which generates non-thermal plasma species, including electrically neutral gas molecules, charged particles in the form of positive ions, negative ions, free radicals and electrons, and quanta of electromagnetic radiation (photons). These non-thermal plasma species are highly reactive and are effective in destroying live pathogens, such as bacteria, viruses and fungi, living in the liquid being treated. Because of the non-thermal nature of reactor 100, reactor 100 preserves the quality and other heat-sensitive attributes of the liquids being pasteurized.

Examples of liquids that can be treated include any liquid that is instillable in a living mammal, such as a human, dog, horse, cat, etc. The term "instillable" includes all liquids that are non-toxic to a living mammal when introduced into the mammal by methods such as oral ingestion, inhaling, transdermal absorption, rectal (as with enema or other such solutions), direct insertion into arterial vessels, venal vessels (IV), lymphatic vessels, the spinal canal, and body cavities such as the abdomen, the lungs or the liver, intramuscular injection, and subcutaneous injection.

One example of such a liquid is a liquid that is capable of being consumed and assimilated by a living mammal as nourishment. Such liquids include water, juices (such as fruit juices), milk, carbonated and non-carbonated soft drinks, flavored non-carbonated beverages, soups and other liquid foods (including liquids with food particles in suspension). Other treatable liquids may include fermentation broth, medications and vaccines of all types, total parenteral nutrition (TPN) liquids, including sugars and lipids, etc., intravenous (IV) fluids such as Lactated Ringers or D5, etc., renal dialyzing fluids (which are instilled and drawn back off), and bodily fluids that must be returned to the body without damage to viable components such as platelets and leukocytes. Such bodily fluids include blood, blood products and cerebrospinal fluid (CSF).

It has been found that the reduction in pathogens living in the liquid being treated is greatly enhanced if fine gas bubbles are introduced into the liquid being treated by the plasma. The interaction of gas bubbles with the plasma has been found to enhance the sterilization effectiveness. The resulting liquid-gas mixture can include a gas dispersed in a liquid or a liquid dispersed in a gas. The gas-can be mixed with the liquid in a variety of ways, such as by diffusion or injection. Various gas injection devices can be used, such as a Venturi tube gas injector made by Mazzei Injector Corporation. Alternatively, the liquid can be sprayed through the reaction chamber to form droplets of liquid separated by gas.

Introducing fine gas bubbles into the liquid greatly enhances the generation of plasma in reactor 100 for killing pathogens living in the liquid being treated. As the gas-liquid mixture is passed through NTP reactor 208, the gas bubbles in the liquid become excited by the applied electric field, generating non-thermal plasma. The non-thermal plasma species then interact with and kill pathogens living in the liquid. Parameters associated with gas injection include composition of the gas, amount and distribution of the gas in the liquid, the size of the gas bubbles, velocity of the liquid relative to the physical motion of the gas, and the gas injector orifice size. Experiments have shown in liquid containing gas bubbles, especially with a gas containing 90% oxygen, bacteria kill is increased substantially as compared to the bacteria kill in liquid containing no gas bubbles.

Various factors that may affect the killing power of the reactive NTP species within reaction volume 106 include the ratio of gas to liquid (from very low to very high), size of gas bubbles, degree of mixing of gas and liquid, and compositions of the gas and liquid. Preferably, the system is adapted to obtain a 5 log to 10 log reduction in pathogens living in the liquid. A high gas-to-liquid ratio can be obtained by injecting the liquid into a gas phase. For example, it was observed that the killing power of the NTP species was greater with smaller gas bubbles than with larger gas bubbles. Also, it has been found that the more evenly the gas bubbles are distributed in the liquid, the more effective the plasma generation and pathogen reduction. In one embodiment, the ratio of gas volume to liquid volume (Gas Volume/Liquid Volume) is preferably 0.1 to 20, more preferably 0.3 to 5, and most preferably 0.5 to 1. However, other ratios outside these ranges can also be used. A variety of gas compositions can be used, such as air, oxygen, ozone and nitrogen, or a mixture of these or other gases. One type of gas may be more effective than the other in a particular application, depending on the type of liquid and the types of pathogens being killed. For example, the gas bubbles can consist of 100% by volume oxygen (e.g., $O_2$) or 100% by volume nitrogen.

Figure 2:
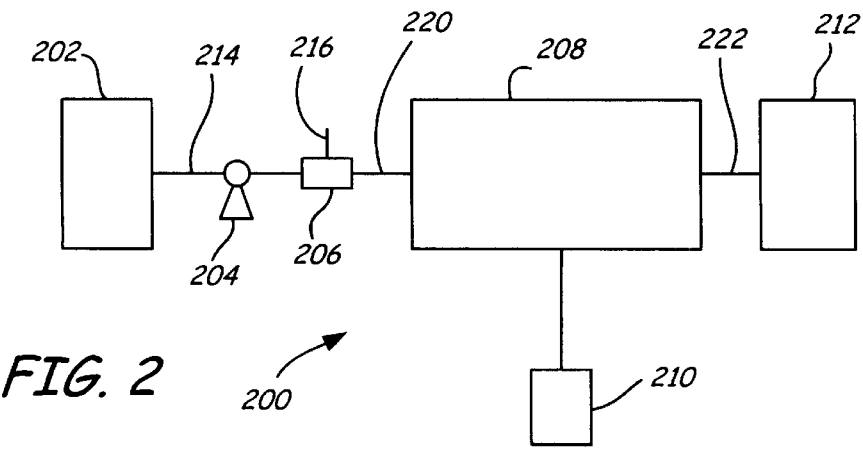
FIG. 2 is a diagram which schematically illustrates a non-thermal plasma liquid pasteurization system, which introduces gas bubbles into the liquid according to one embodiment of the present invention.

FIG. 2 is a diagram which schematically illustrates a non-thermal plasma liquid pasteurization system 200, which introduces gas bubbles into the liquid according to one embodiment of the present invention. System 200 includes liquid source tank 202, pump 204, gas mixing device 206, non-thermal plasma reactor 208, high voltage power supply 210 and liquid receiving tank 212. Source tank 202, pump 204, gas mixing device 206, non-thermal plasma reactor 208 and receiving tank 212 are coupled in series with one another within a treatment flow path 214, which can be formed of a series of tubes or other liquid channels for passing the liquid to be treated from one element in path 214 to the next.

Tank 202 contains the liquid to be treated. Pump 204 pumps liquid from tank 202 to tank 212, through treatment flow path 214. Additional pumps can be placed at various locations along treatment flow path 214 in alternative embodiments. Also, pump 204 can be eliminated in embodiments in which another mechanism, such as gravity, is used for moving the liquid along treatment flow path 214. The output of pump 204 is coupled to the input of gas mixing device 206. The flow rate of the pump is set based on factors such as the desired treatment time, the applied voltage, the dimensions/structures of reactor 208, and the size of gas mixing device 206. Gas mixing device 206 can include any device that is capable of introducing gas bubbles into the liquid flowing through treatment flow path 214. Various mixing devices can be used, such as a gas diffuser or a gas injector. In one embodiment, gas mixing device 206 includes a Venturi tube injector. Other types of gas mixers can also be used. Gas mixing device 206 has a gas inlet 216 for receiving the gas to be mixed into the liquid.

The gas-liquid mixture is then provided to liquid inlet 220 of non-thermal plasma reactor 208. Reactor 208 can include reactor 100 shown in FIG. 1, for example. High voltage power supply 210 is electrically coupled to the electrodes within reactor 208. As the gas-liquid mixture passes through reactor 208, from liquid inlet 220 to liquid outlet 222, the non-thermal plasma generated in reactor 208 pasteurizes the liquid by destroying at least a portion of the live pathogens living in the liquid. The treated liquid then exits through liquid outlet 222 and is collected in receiving tank 212.

In one embodiment, the liquid being treated within reactor 208 is kept under a pressure that is greater than an ambient pressure surrounding the reactor so as to maintain the gas bubbles substantially uniformly distributed in the liquid and of a small size. The pressure can be increased by providing liquid outlet 222 with a cross-sectional area that is less than the cross-sectional area of liquid inlet 222. Also, the internal reactor flow path can be designed to provide a back pressure in the liquid and to provide turbulent flow.

Figure 3:
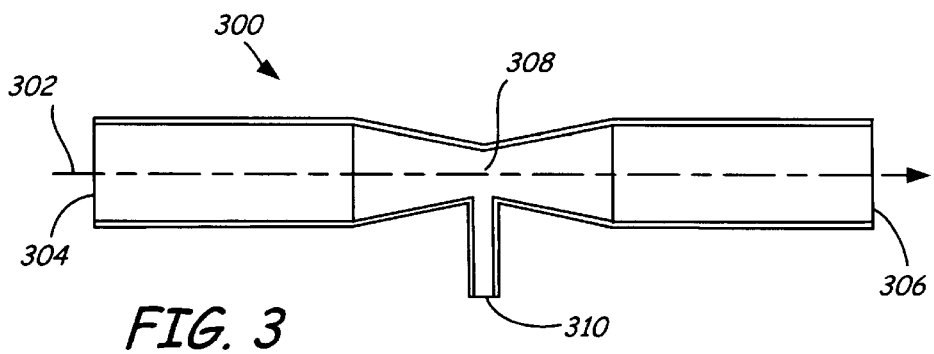
FIG. 3 is a diagram illustrating a Venturi tube injector, which can be used for introducing gas bubbles within the system shown in FIG. 2.

FIG. 3 is a diagram illustrating a Venturi tube injector 300, which can be used for the gas mixing device 204 shown in FIG. 2. Injector 300 has a main flow path 302 between an inlet 304 and an outlet 306 and has a flow constriction 308. A gas inlet 310 is coupled to the main flow path 302 at the flow constriction 308. As liquid flows along main flow path 302 a pressure difference between inlet 304 and outlet 306 creates a vacuum inside the injector body, which draws gas into the injector through gas inlet 310 and results in a mixture of gas and liquid at outlet 306. A Venturi tube injector is a high efficiency, differential pressure injector it has been found that this type of injector mixes gases with liquids very well. As a result, bubbles in the gas-liquid mixture produced at the output of injector 300 are extremely fine and uniformly distributed.

Figure 4:
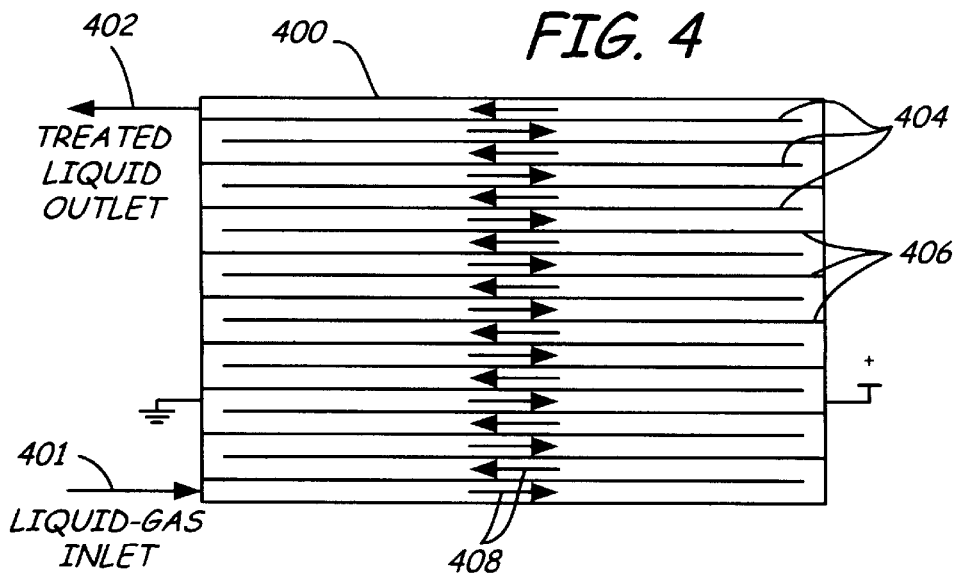
FIG. 4 is a diagram which schematically illustrates a cross-sectional view of a non-thermal plasma reactor which has a winding, serpentine flow path, according to one embodiment of the present invention.

FIG. 4 is a diagram which schematically illustrates a cross-sectional view of a non-thermal plasma reactor which has a winding, serpentine flow path and can be used for reactor 208 (shown in FIG. 2) according to one embodiment of the present invention. Reactor 400 includes a liquid-gas inlet 401, a treated liquid-gas outlet 402 and a plurality of oppositely polarized non-thermal plasma electrodes 404 and 406 which are arranged to form a serpentine liquid flow path indicated by arrows 408. As described above, each electrode 404 and 406 is physically and electrically isolated from the liquid flow path by a respective dielectric barrier. In one embodiment, electrodes 404 and 406 are each formed as a planar electrode panel that is parallel to and separated from the other electrode panels. Each electrode panel 404 and 406 has a polarity that is opposite to the polarity of the next adjacent electrode panel. This creates a plurality of reaction volumes which are coupled together in series to form flow path 408. Each reaction volume is defined by the gap between a respective pair of electrodes 404 and 406. The serpentine flow path can be used to increase the liquid residence time within reactor 400 and to increase the turbulence of the liquid flow, which may assist in keeping the gas bubbles more evenly distributed and of a small size in the liquid. Any number of reaction volumes can be used in alternative embodiments. For example, reactor 400 can include a single reaction volume such as shown in FIG. 1, two reaction volumes that form a U-shaped flow path, or a plurality of reaction volumes as shown in FIG. 4. In an alternative embodiment, the individual reaction volumes extend parallel to one another from inlet 401 to outlet 402.

Figure 5:
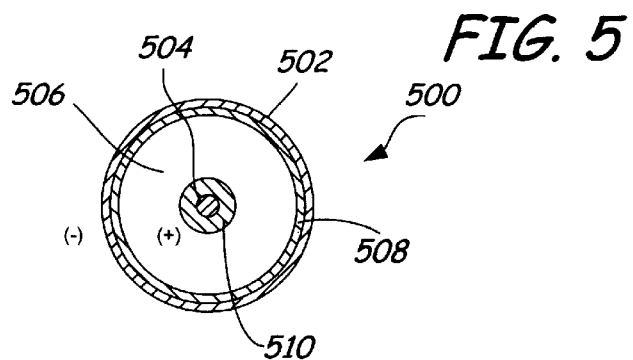
FIG. 5 is a cross-sectional view of a tubular non-thermal plasma reactor according to an alternative embodiment of the present invention.

FIG. 5 is a cross-sectional view of a tubular non-thermal plasma reactor 500 according to an alternative embodiment of the present invention. Reactor 500 has a tubular structure, with flow going into or out of the page in FIG. 5. Reactor 500 includes a tubular ground electrode 502 and a wire high voltage electrode 504, which is coaxial with electrode 502. In an alternative embodiment, electrode 502 is a high voltage electrode and electrode 504 is a ground electrode. Electrodes 502 and 504 are separated by a gap which defines a reaction volume 506. Electrodes 502 and 504 are physically and electrically isolated from reaction volume 506 by respective dielectric barriers 508 and 510. Dielectric barriers 508 and 510 prevent electrodes 502 and 504 from contaminating the liquid being treated and provide electrical isolation that prevents the liquid within reaction volume 506 from shorting electrode 502 to electrode 504.

Figure 6:
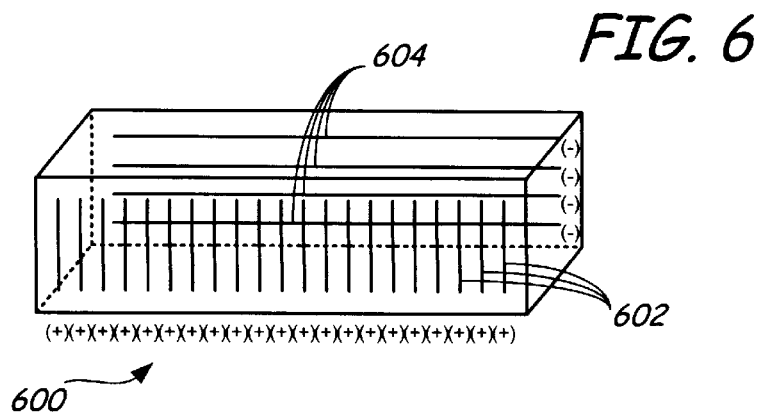
FIG. 6 is a perspective view of a non-thermal plasma reactor having narrow strip electrodes.

FIG. 6 is a perspective, schematic view of a non-thermal plasma reactor 600 having narrow strip electrodes 602 and 604. Electrodes 602 are biased at one polarity, and electrodes 604 are biased at an opposite polarity. Electrode strips 602 and 604 are arranged perpendicular to one another and are spaced about a reaction volume. Each individual electrode 602 and 604 is insulated by a dielectric barrier. For example, all of the electrodes 602 can be embedded within one sheet of dielectric material, and all of the electrodes 604 can be embedded within another sheet of dielectric material. With this type of electrode structure, the local electric fields around electrodes 602 and 604 are greatly enhanced, which ensures discharge takes place easily and effectively in the gas bubbles.

Figure 7A:
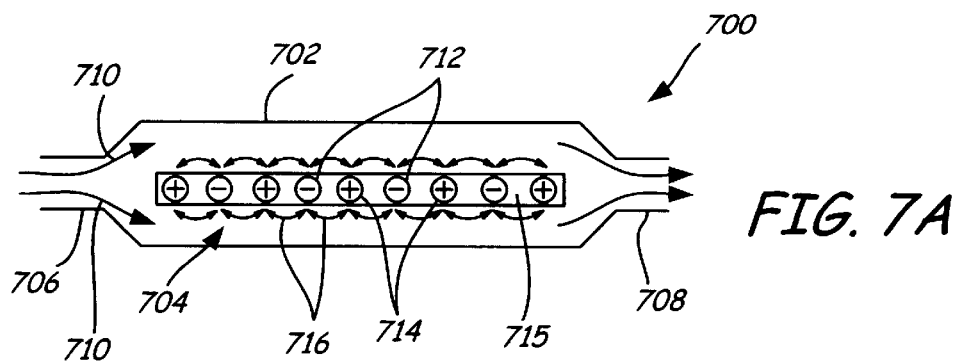
FIG. 7A is a side plan view of a surface discharge-type non-thermal plasma reactor according to another alternative embodiment of the present invention.

FIG. 7A is a side cross-sectional view of a non-thermal plasma reactor 700 according to another alternative embodiment of the present invention. Reactor 700 includes a housing 702 and at least one "surface" discharge electrode 704. Housing 702 has a liquid inlet 706, a liquid outlet 708 and a pair of flow paths 710 extending on either side of surface discharge electrode 704. Surface discharge electrode 704 includes a plurality of adjacent conductors 712 and 714 having opposite polarity. Conductors 712 and 714 are electrically insulated from flow paths 710 by a dielectric material 715. In one embodiment, conductors 712 and 714 are each individually coated with a dielectric material that forms an electrically insulating sheath. In an alternative embodiment, conductors 712 and 714 are embedded in a dielectric material to form an electrode sheet. Conductors 712 and 714 can have diameters of about 0.1 to about 3.0 millimeters, for example, and are each separated by a gap in the range of 0 to 6 millimeters, for example.

Figure 7B:
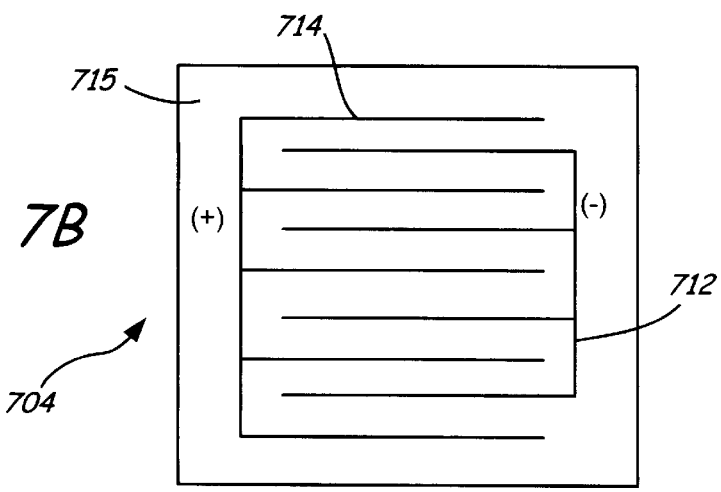
FIG. 7B is a plan view of a surface discharge electrode used in the reactor shown in FIG. 7A.

Excitation of conductors 712 and 714 generates microcurrent electric field discharge paths 716 along the surfaces of electrode 704. Electric field discharge through discharge paths 716 generate non-thermal surface plasma species within the liquid being treated, along the surface of electrode 704. These non-thermal surface plasma species are highly reactive and destroy pathogens living in the liquid, similar to the embodiments discussed above. Electrode 704 can have a variety of shapes, such as planar or tubular. FIG. 7B is a plan view of electrode 704 in planar form, which illustrates one possible arrangement of conductors 712 and 714.

Figure 8:
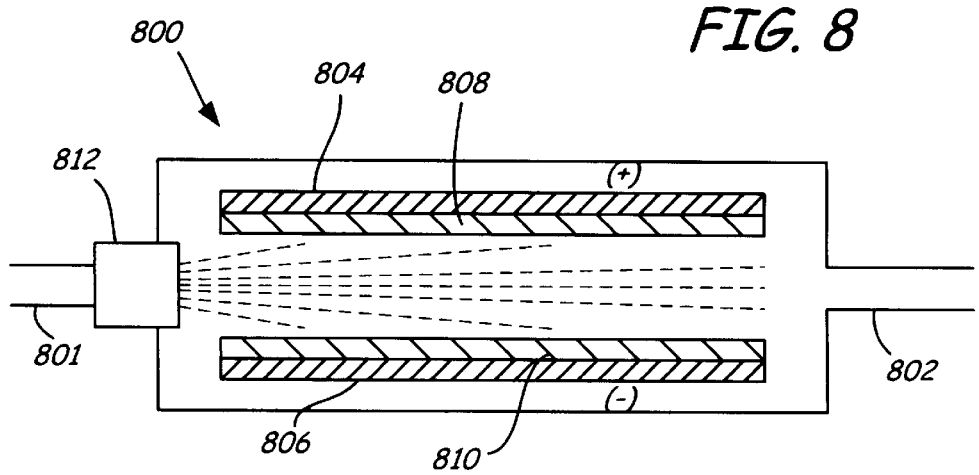
FIG. 8 is a side view of a non-thermal plasma reactor in which the liquid is sprayed into the reaction volume, according to another alternative embodiment of the present invention.

FIG. 8 is a side view of a non-thermal plasma reactor 800 according to another alternative-embodiment of the present invention. Reactor 800 includes fluid inlet 801, fluid outlet 802, electrodes 804 and 806 and dielectric barriers 808 and 810. Electrodes 804 and 806 are separated from one another by a gap, which defines a reaction volume between dielectric barriers 808 and 810. Reactor 800 further includes a sprayer 812 which is coupled to fluid inlet 801 for receiving the liquid to be treated. Sprayer 812 spays the liquid through the reaction volume, between dielectric barriers 808 and 810 to form a fine mist within the reaction volume. The treated liquid then exits through liquid outlet 802. Sprayer 812 assists in generating a gas-liquid mixture within the reaction volume, which helps the plasma in destroying pathogens living in the liquid.

Figure 9:
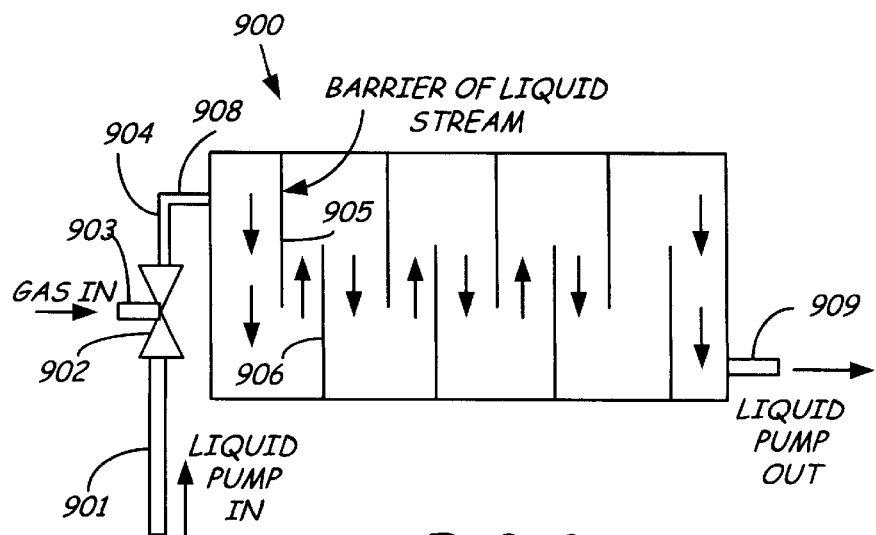
FIG. 9 illustrates a non-thermal plasma reactor having a set of barriers used to increased back pressure within the liquid being treated.
Figure 10:
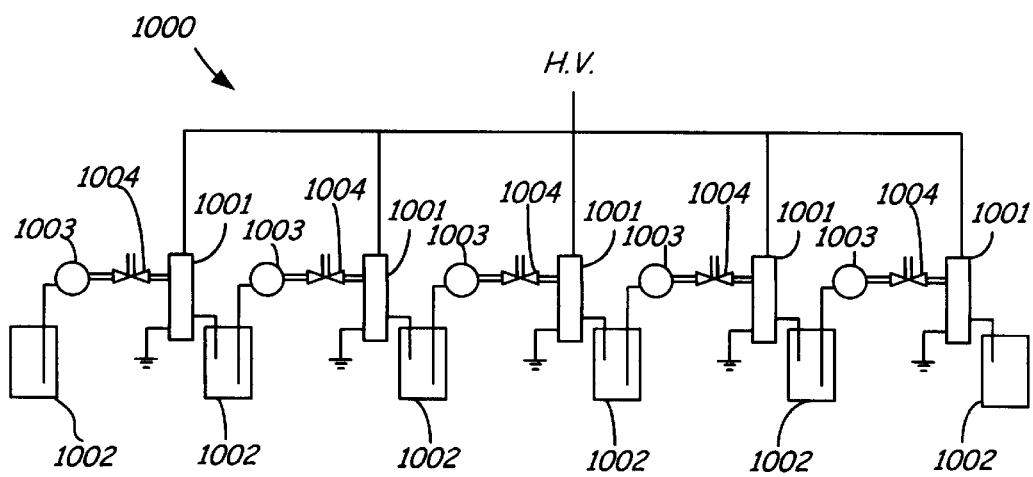
FIG. 10 is a diagram of a pasteurization system having five NTP reactors connected together in series.
Figure 11:
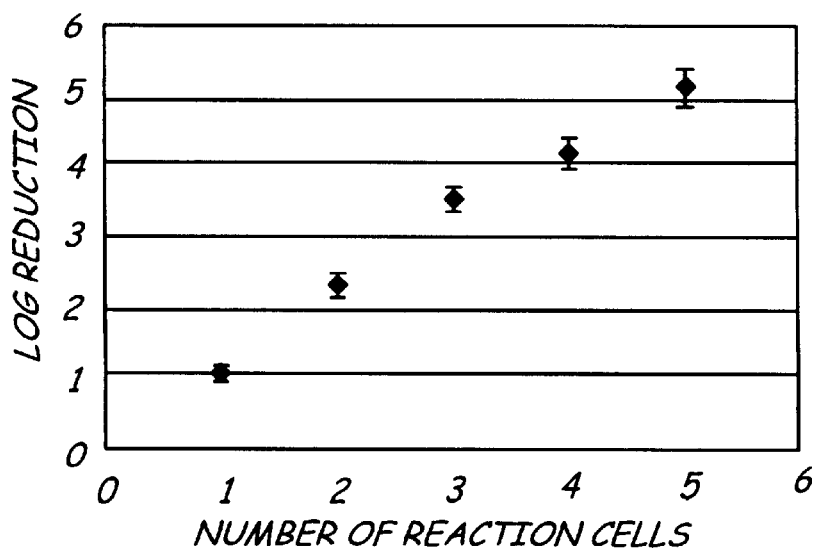
FIG. 11 is a graph illustrating the log Salmonella bacterial reduction in liquid as a function of the number of NTP reactors in-the system shown in FIG. 10.
Figure 12:
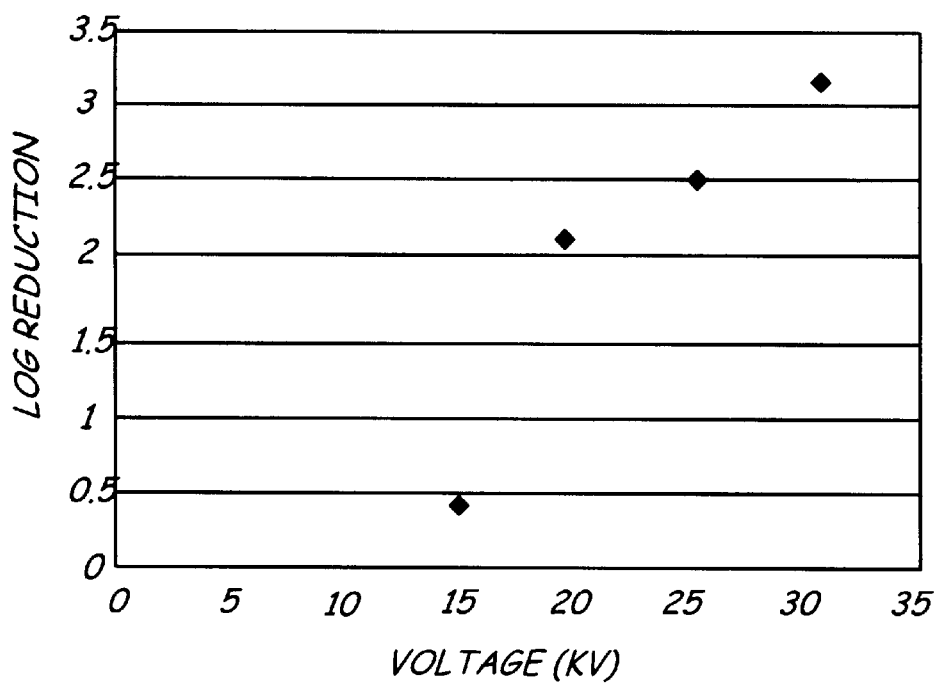
FIG. 12 shows the log reduction in Salmonella bacteria as a function of the voltage applied to each NTP reactor within the system shown in FIG. 10.
Figure 13:
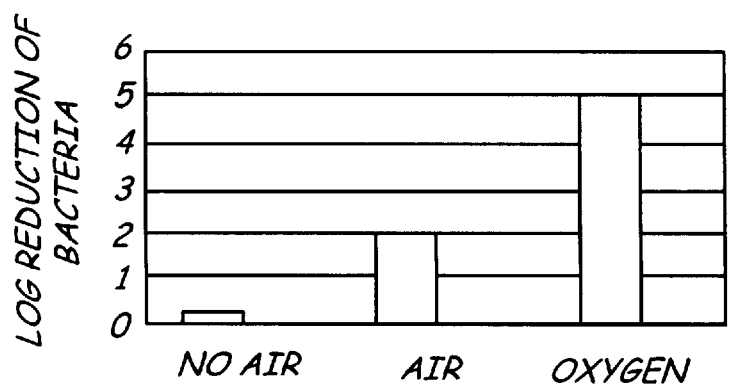
FIG. 13 is a graph illustrating the log reduction of bacteria as a function of the type of gas injected in the liquid within the system shown in FIG. 10.
Figure 14:
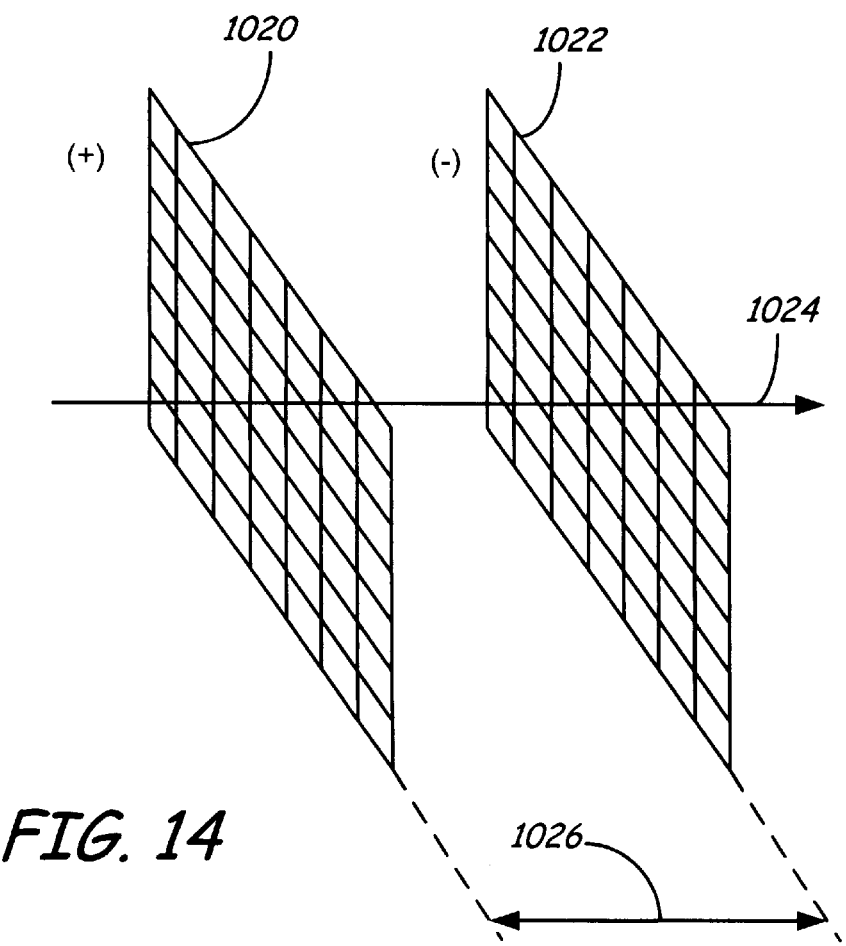
FIG. 14 is a simplified, perspective view of two mesh-type non-thermal plasma electrodes that can be used for pasteurizing liquids according to another alternative embodiment of the present invention.

FIG. 9 illustrates an NTP reactor 900 having a set of barriers used to increased the back pressure within the liquid being treated. Briefly referring back to FIG. 2, the stream of the gas-liquid mixture from gas mixing device 206 to reactor 208 is of high speed and high pressure. To some extent, the distribution of gas bubbles in the liquid depends on the back pressure of the mixture. The higher the back pressure, the higher the solubility of the gas in the liquid. In one embodiment, a large tank 202 can be used to increase the back pressure in the system.

In the embodiment shown in FIG. 9, the arrangement of electrode panels is used to increase the back pressure. As liquid is pumped through tube 901, gas injector 902 draws gas into gas inlet 903 and produces a gas-liquid mixture at the outlet of the injector. Tube 904 delivers the gas-liquid mixture from gas injector 902 to inlet 908 of NTP reactor 900. NTP reactor 900 has a plurality of electrode plates 905 and 906, which are arranged to form a serpentine flow path from inlet 908 to outlet 909 and are arranged perpendicular to inlet 908. With this arrangement, electrode plates 905 and 906 form barriers to the liquid stream entering from inlet 908 and being passed from one portion of the flow path to the next. These barriers further increase back pressure within the gas-liquid mixture.

Experimental Results

Several experiments were performed to demonstrate the effectiveness of non-thermal plasma in reducing pathogens living in a liquid. These experiments are described below.

Experiment 1

The first experiment was performed to test the effect of air injection conditions and applied electric field on the viability of Salmonella in a liquid carrier (i.e., distilled water).

In a first test a "static" reactor was used, which had stripped electrodes similar to the electrodes shown in FIG. 6. In the static reactor, the liquid to be treated was placed into the reactor with no flow. The gaps between individual electrode strips were 10mm, and the effective reaction volume had a gap of 7 mm. A liquid containing Salmonella and no gas bubbles was placed in the reaction volume. The liquid was then treated by operating the electrodes at 25 kV. Next, a liquid containing Salmonella was placed in the reaction volume and bubbled with air at 1–2 CFH to introduce air bubbles into the liquid. The electrodes were again operated at 25 kV. Finally, a liquid containing Salmonella was placed into the reaction volume and bubbled with oxygen at 1–2 CFH. The electrodes were again operated at 25 kV.

Table 1 shows that the reduction in bacteria is minimal when there are no gas bubbles in the liquid and is increased substantially with the presence of air bubbles and especially with the presence of oxygen bubbles, in the liquid.

TABLE 1

| Treatment Time (minutes) | 1–2 | 3–4 | 5 |
| --- | --- | --- | --- |
| Reduction (logs) without air bubbles | 0.5 | 0.8 | 1.2 |
| Reduction (logs) with air bubbles | 2 | 3 | 3–4 |
| Reduction (logs) with oxygen bubbles | 3–4 | 5 | >5 |

The reductions in bacterial load were evaluated using standard approaches involving serial dilutions of a solution which were plated onto culture plates. Following incubation, colonies were counted to evaluate the number of organisms in the diluted solutions. Using the dilution values, estimates were obtained of the original bioload.

Next, Salmonella reduction was tested with a "static" NTP reactor having oppositely polarized plate electrodes, which were operated at 15 kV and were separated by dielectric barriers. The gap between the electrodes was 10 mm, and the effective reaction volume between the dielectric barriers had a gap of 7 mm. Liquid containing Salmonella was placed in the reaction volume, bubbled with air and treated. The resulting bacteria reduction as a function of time is shown in Table 2.

TABLE 2

| | | | | | |
|---|---|---|---|---|---|
| Time (min) | 5 | 10 | 15 | 20 | 25 |
| Reduction (logs) | 2 | 2.5 | 3 | 5 | >5 |

The smaller applied voltage, as compared to the voltage used to produce the results in Table 1, resulted in a smaller log reduction of Salmonella bacteria in the liquid.

Next, Salmonella reduction was tested by placing a liquid containing Salmonella into the reaction volume, bubbling the liquid with oxygen and then treating the liquid-oxygen mixture by operating the electrodes at 15 kV. Again, the gap between the electrodes was 10 mm, with an effective reaction volume gap of 7 mm. The results of this test are shown in Table 3.

TABLE 3

| | | | |
|---|---|---|---|
| Time (min) | 5 | 10 | 15 |
| Reduction (logs) | 3 | 4 | >5 |

Looking at Tables 1–3, the use of non-thermal plasma to treat a liquid having injected gas bubbles is effective in achieving at least a five log reduction in Salmonella. Comparing Tables 2 and 3, the use of oxygen bubbles as compared to air bubbles increased the amount of Salmonella reduction per unit of treatment time.

Experiment 2

In the second experiment, the use of non-thermal plasma was tested for effectiveness in killing *E. Coli* bacteria within a liquid. The test apparatus used in the second experiment was similar to that shown in FIG. 2. The gas mixing device included a Venturi tube injector, which introduced air and oxygen at 1–2 CFH, and the NTP reactor had a serpentine flow path such as that shown in FIG. 4 with two individual reaction volumes. The gaps between the electrodes in the reactor was 10 mm, and the effective reaction volume between the dielectric barriers had a gap of 7 mm. An untreated liquid inoculated with five logs of *E. Coli* was placed in tank 202 and passed through NTP reactor 208 to tank 212. Samples were then taken from the untreated liquid in tank 202 and the treated liquid in tank 212 and cultured in a similar fashion as described above with reference to Table 1. Bacterial colonies were found in the cultured untreated samples, while no bacterial colonies were observed in the cultured treated samples. Based on these observations, it was concluded that the pasteurization system shown in FIG. 2 was effective in producing a five log reduction in *E. Coli.*

Experiment 3

In the third experiment, the NTP pasteurization system shown in FIG. 10 was built and tested. System 1000 included five NTP reactors 1001 connected together in series with each NTP reactor 1001 having its own source tank 1002, pump 1003 and gas injector 1004. The outlet of each NTP reactor 1001 was coupled to the source tank 1002 of the next reactor 1001 in the series. The plurality of gas injectors 1004 ensured that the gas-liquid mixture contained sufficiently fine bubbles throughout the flow. Air was injected through each injector 1004 at 2 cubic feet per hour (CFH). Pumps 1003 pumped the liquid through system 1000 at 10 gallons per hour. The electrical connections to the NTP reactors 1001 were coupled together in parallel with one another and were excited at 20 kV. The number of NTP reactors 1001 in system 1000 was varied so that the effect of the number of reactors on Salmonella bacterial reduction could be examined.

FIG. 11 is a graph illustrating the log Salmonella bacterial reduction in the liquid as a function of the number of NTP reactors 1001 in FIG. 10. With five NTP reactors 1001, a five log bacterial reduction was be obtained with the system shown in FIG. 10. However, this five log bacterial reduction was not observed when only one gas injector was used prior to the first NTP reactor in the system. This suggests the importance of gas bubbles in the liquid. Looking at FIG. 11 the log bacterial reduction increased with the number of NTP reactors. This increase can be attributed to both the increased energy input and the increased amount of air bubbles in the liquid.

Experiment 4

In the fourth experiment, the log reduction of Salmonella bacteria was tested as a function of applied voltage. The same system was used in Experiment 4 as was used in Experiment 3, with five NTP reactors connected together in series. Experiment 4 was conducted at 30 gallons per hour, and with 2 CFH air injection in each injector 1004. FIG. 12 shows the log reduction in Salmonella bacteria as a function of the voltage applied to each NTP reactor 1001. As can be seen from FIG. 12, log reduction in bacteria increases with increasing applied voltage. More than three logs of bacterial reduction is achieved at 30 kV.

Experiment 5

In the fifth experiment, the pasteurization system shown in FIG. 10 and described above in Experiment 3 was used under three conditions: (1) without air injection; (2) with air injection; and (3) with oxygen injection. Otherwise, the same operating conditions were used as were used in Experiment 3, with five NTP reactors 1001 connected together in series. If oxygen can be replaced with clean air, the equipment and running costs of the system can be reduced. The results of Experiment 4 are shown in the graph of FIG. 13. FIG. 13 is a graph illustrating the log reduction of Salmonella bacteria for each of the test. conditions. As shown in FIG. 13, without any air or gas input into the system, the system was only partially effective in killing Salmonella. With air injection, a two log reduction of bacteria was achieved. With oxygen injection, a five log reduction of bacteria was achieved. This suggests that air is a possible gas media in the NTP pasteurization system, but modifications of the system shown in FIG. 10 may be needed to achieve a five log reduction with air injection. For example, the resident time of the treated liquid within NTP reactors 1001 can be increased.

FIG. 14 is a simplified, perspective view of two mesh-type non-thermal plasma electrodes 1020 and 1022 that can be used for pasteurizing liquids according to another alternative embodiment of the present invention. Electrodes 1020 and 1022 are each formed of a conductive wire mesh which has been coated with a dielectric material such that the wire mesh is electrically insulated from the liquid being treated. The dielectric coating is formed so that the area between each conductive segment in the mesh is open to fluid flow. Any coating technique can be used, such as physical vapor deposition (PVD) or chemical vapor deposition (CVD).

The liquid to be treated is passed through electrodes 1020 and 1022 in the direction of arrow 1024, substantially perpendicular to the planes formed by electrodes 1020 and 1022. As the liquid passes through meshes 1020 and 1022, electrodes 1020 and 1022 are electrically coupled to opposite voltage potentials which creates a plasma within gap 1026 for treating the liquid present within the gap. If the openings in electrodes 1020 and 1022 are sufficiently small, the openings can further assist in breaking-up larger gas bubbles and maintaining the gas bubbles in the liquid at a sufficiently small size. Other arrangements can also be used, and meshes 1020 and 1022 can be non-planar. Also, a series of electrode pairs 1020 and 1022 can be used, wherein the liquid flows sequentially through each electrode pair for treatment. In an alternative embodiment, a gas injector or diffuser is not used to mix the gas and liquid. Rather, the gas is supplied through a tube into the reactor and is then broken into small bubbles as the gas and liquid are forced through the small openings in the mesh electrodes.

In summary, experiments have shown that non-thermal plasma is effective in reducing viable bacteria in a liquid sample. Non-thermal plasma can therefore be used for at least partially sterilizing liquid food such as juices and milk. Since there is substantially no ohmic heating, energy consumption during non-thermal plasma sterilization is small, and there is no need to cool the liquid being treated. This allows the system to be easily scaled-up accommodate a very large treatment volume. The desired treatment time can be obtained by passing the liquid through multiple NTP reactors connected together in series with one another or by cycling the liquid through the same reactor multiple times. Also, the number of series-connected reaction volumes in the same reactor can be increased or decreased. Because of the non-thermal nature of the system, the system preserves the quality and other heat-sensitive-attributes of the liquid, such as taste and vitamin content. Other possible applications include pasteurization/sterilization of fermentation broth, biological fluids, blood products, medicines and vaccines. Also, since each electrode is physically and electrically isolated from the liquid being treated, the electrodes do not act as a source of contaminants to the liquids.

Although the present invention has been described with reference to preferred embodiments, workers skilled in the art will recognize that changes may be made in form and detail without departing from the spirit and scope of the invention.

What is claimed is:

1. A method of at least partially sterilizing a liquid comprising living pathogens, the method comprising:
   (a) mixing the liquid comprising living pathogens with a gas to form a liquid-gas mixture; and
   (b) treating the liquid-gas mixture in a reaction volume by generating a non-thermal plasma within the reaction volume and thereby killing at least a portion of the pathogens within the liquid of the liquid-gas mixture.

2. The method of claim 1 wherein:
   step (a) comprises mixing a living-mammal-instillable liquid comprising living pathogens with the gas; and
   step (b) comprises killing at least a portion of the pathogens within the living-mammal-instillable liquid with the non-thermal plasma.

3. The method of claim 2 wherein the living-mammal-instillable liquid comprises a liquid food that is capable of being consumed and assimilated by a living mammal as nourishment.

4. The method of claim 1 wherein the: living-mammal-instillable liquid is selected from the group consisting of water, juices, milk, soft drinks, favored non-carbonated beverages, and soups.

5. The method of claim 1 wherein step (b) comprises reducing an amount of the pathogens living in the liquid by at least a 5 log reduction.

6. The method of claim 1 wherein step (a) comprises pumping the liquid through the reaction volume.

7. The method of claim 1 wherein step (a) comprises spraying the liquid through the reaction volume.

8. The method of claim 1 wherein step (a) comprises introducing gas bubbles into the liquid to generate the liquid-gas mixture.

9. The method of claim 8 and further comprising:
   (c) maintaining the gas bubbles substantially uniformly distributed in the liquid during step (b).

10. The method of claim 9 wherein step (c) comprises:
    (c) (1) maintaining the liquid within the reaction volume under a pressure that is greater than an ambient pressure.

11. The method of claim 8 wherein step (a) comprises:
    (a) (1) passing the liquid through a main flow path of a venturi tube mixer; and
    (a) (2) introducing the gas into a gas inlet of the venturi tube mixer, which is coupled to the main flow path, so as to mix the gas into the liquid.

12. The method of claim 8 wherein the liquid-gas mixture has a ratio of gas volume to liquid volume of 0.1 to 20.

13. The method of claim 8 wherein the gas bubbles comprise a gas selected from the group consisting of air, oxygen, ozone and nitrogen.

14. The method of claim 8 wherein the gas bubbles consist of 100% by volume $O_2$.

15. The method of claim 1 wherein step (b); comprises:
    (b)(1) generating the plasma with a non-thermal plasma reactor having at least one non-thermal plasma electrode adjacent to the reaction volume; and
    (b)(2) physically isolating and,electrically insulating the liquid from all of the non-thermal plasma electrodes in the non-thermal plasma reactor with at least one dielectric barrier.

16. The method of claim 15 wherein step (b) further comprises:
    (b) (3) passing the liquid through an inlet of the non-thermal plasma reactor, wherein the inlet has a first cross-sectional area; and
    (b) (4) passing the liquid through an outlet of the non-thermal plasma reactor after the liquid has been treated by the plasma, wherein the outlet has a second cross-sectional area that is smaller than the first cross-sectional area.

17. The method of claim 1 wherein step (b) comprises generating the non-thermal plasma within multiple non-thermal plasma reactors which are coupled in series with one another, passing the liquid-gas mixture through the multiple non-thermal plasma reactors and changing a number of the multiple non-thermal plasma reactors based on a desired level of reduction in an amount of the pathogens living in the liquid.

18. The method of claim 1 wherein:
    step (b) comprises generating the non-thermal plasma with a non-thermal plasma reactor having first and second mesh electrodes which oppose one another about the reaction volume, and applying different voltage potentials to the first and second mesh electrodes to generate the non-thermal plasma within the reaction volume; and step (a) comprises passing the liquid-gas mixture through openings in the first mesh electrode, through the reaction volume and then through openings in the second mesh electrode.

19. A liquid food pasteurization apparatus comprising:

a liquid food input;

a treatment flow path coupled to the liquid food input;

a pump coupled to the treatment flow path for pumping liquid food from the liquid food input through the treatment flow path;

a gas injector coupled in the treatment flow path and having a gas inlet for receiving a gas to be injected into the liquid food; and a non-thermal plasma reactor coupled in the treatment flow path and comprising a liquid food inlet, a liquid food outlet, a reaction volume between the liquid food inlet and the liquid food outlet and at least one non-thermal plasma electrode adjacent to the reaction volume, wherein each non-thermal plasma electrode is isolated physically and electrically from the flow path by a dielectric barrier.

20. The liquid food pasteurization apparatus of claim 19 wherein the gas injector comprises a venturi tube gas mixer having a main flow path, which is coupled in series with the treatment flow path, and a flow constriction in the main flow path, which is coupled to the gas inlet.

21. The liquid food pasteurization apparatus of claim 19 wherein the non-thermal plasma reactor comprises a volume discharge reactor having:

a ground electrode;

a high-voltage electrode, which is parallel to the ground electrode and is separated from the ground electrode panel by a gap, a first dielectric barrier positioned between the ground electrode and the gap;

a second dielectric barrier positioned between the high-voltage electrode and the gap; and a discharge path, which extends from the ground electrode to the high-voltage electrode, across the gap, wherein the treatment flow path extends through the gap and across the discharge path.

22. The liquid food pasteurization apparatus of claim 21 wherein the ground electrode and the high-voltage electrode are planar.

23. The liquid food pasteurization apparatus of claim 21 wherein at least one of the ground electrode and the high-voltage electrode is tubular and coaxial with the other of the ground electrode and the high-voltage electrode.

24. The liquid food pasteurization apparatus of claim 19 wherein the non-thermal plasma reactor comprises a surface discharge reactor having:

a liquid flow path extending through the reaction volume;

a surface discharge electrode which comprises first and second oppositely polarized conductors, which are spaced from one another laterally along a discharge surface that is parallel and adjacent to the liquid flow path, and defines a surface discharge path which extends between the first and second conductors, along the first discharge surface; and a dielectric barrier positioned between the liquid flow path and the first and second conductors.

25. The liquid food pasteurization apparatus of claim 19 wherein the liquid food inlet has a first cross-sectional area and the liquid food outlet has a second cross-sectional area that is smaller than the first cross-sectional area.

26. The liquid food pasteurization apparatus of claim 19 wherein the treatment flow path has a serpentine flow pattern within the reaction volume that is arranged to generate turbulent flow within the reaction volume.

27. The liquid food pasteurization apparatus of claim 19 wherein:

the non-thermal plasma reactor comprises first and second mesh electrodes which are spaced parallel to one another on opposite sides of the reaction volume, wherein the first and second mesh electrodes each include a conductive mesh, a dielectric coating on the conductive mesh and a plurality of openings extending through the conductive mesh and the dielectric coating; and the treatment flow path extends through the plurality of openings in the first mesh electrode, through the reaction volume and then through the plurality of openings in the second mesh electrode.

28. A liquid food pasteurization apparatus comprising:

a liquid food input for receiving a liquid food comprising pathogens living in the liquid food;

means for introducing gas bubbles into the liquid food received from the liquid food input to produce a mixture of the liquid food and the gas bubbles; and non-thermal plasma reactor means for receiving the mixture of the liquid food and the gas bubbles within a reaction volume and for generating a non-thermal plasma within the reaction volume to thereby kill at least a portion of the pathogens within the liquid food.

* * * * *

UNITED STATES PATENT AND TRADEMARK OFFICE
CERTIFICATE OF CORRECTION

PATENT NO. : 6,562,386 B2
DATED : May 13, 2003
INVENTOR(S) : Ruan et al.

It is certified that error appears in the above-identified patent and that said Letters Patent is hereby corrected as shown below:

<u>Column 12,</u>
Line 5, delete ":" appearing after the word "the".
Line 38, delete ";" appearing after the letter "(b)".
Line 42, delete "," appearing after the word "and".

Signed and Sealed this

Sixteenth Day of March, 2004

JON W. DUDAS
*Acting Director of the United States Patent and Trademark Office*